United States Patent [19]

Agrawal et al.

[11] Patent Number: 4,876,377
[45] Date of Patent: * Oct. 24, 1989

[54] ALKYLATION OF AROMATIC AMINES WITH OLEFINS ON PARTIALLY DEALUMINATED ZEOLITES

[75] Inventors: Rakesh Agrawal; Steven R. Auvil, both of Allentown, Pa.; Michel Deeba, North Brunswick, N.J.

[73] Assignee: Air Products and Chemicals, Inc., Allentown, Pa.

[*] Notice: The portion of the term of this patent subsequent to Apr. 26, 2005 has been disclaimed.

[21] Appl. No.: 171,602

[22] Filed: Mar. 22, 1988

Related U.S. Application Data

[63] Continuation-in-part of Ser. No. 796,465, Nov. 8, 1985, Pat. No. 4,740,620, and a continuation-in-part of Ser. No. 848,000, Apr. 2, 1986, abandoned.

[51] Int. Cl.$^4$ ............................................. C07C 87/452
[52] U.S. Cl. ..................................... 558/416; 558/418; 558/419; 564/307; 564/309; 564/315; 564/330; 564/409
[58] Field of Search ............... 564/409, 307, 309, 315, 564/330; 558/416, 418, 419; 502/73; 585/446

[56] References Cited

U.S. PATENT DOCUMENTS

| | | | |
|---|---|---|---|
| 2,762,845 | 9/1956 | Stroh et al. | 260/578 |
| 3,178,365 | 4/1965 | Miale et al. | 208/120 |
| 3,275,690 | 9/1966 | Stroh et al. | 260/576 |
| 3,281,483 | 10/1966 | Benesi et al. | 260/672 |
| 3,493,519 | 2/1970 | Kerr et al. | 252/455 |
| 3,506,400 | 4/1970 | Eberly, Jr. et al. | 23/182 |
| 3,649,693 | 3/1972 | Napolitano | 260/578 |
| 3,761,396 | 9/1973 | Pickert et al. | 208/111 |
| 3,923,892 | 12/1975 | Klopfer | 260/578 |
| 3,937,791 | 2/1976 | Garwood | 423/328 |
| 4,259,537 | 3/1981 | Chu | 585/467 |
| 4,393,262 | 7/1983 | Kaeding | 585/467 |
| 4,395,372 | 7/1983 | Kluttz et al. | 260/465 R |
| 4,740,620 | 4/1988 | Dixon et al. | 564/330 |

FOREIGN PATENT DOCUMENTS

| | | | |
|---|---|---|---|
| 1051271 | 7/1955 | Fed. Rep. of Germany | . |
| 1406739 | 7/1964 | France | . |
| 56-110652 | 2/1980 | Japan | . |
| 6407636 | 7/1964 | Netherlands | . |
| 414574 | of 0000 | United Kingdom | . |
| 846226 | 8/1960 | United Kingdom | 564/409 |

*Primary Examiner*—Richard L. Raymond
*Assistant Examiner*—Raymond Covington
*Attorney, Agent, or Firm*—Russell L. Brewer; James C. Simmons; William F. Marsh

[57] ABSTRACT

This invention pertains to an improved process for the alkylation of aromatic amines. The improvement resides in the use with particular aromatic amines and olefins a catalyst which is a highly acidic partially dealuminated zeolite having an increased silica to alumina molar ratio over the original zeolite and an acidity factor of at least 0.3. The partially dealuminated zeolites are preferably exchanged with hydrogen or rare earth metal and are particularly effective for producing an alkylated aromatic amine where the alkyl group is ortho to the amine. The highly acidic partially dealuminated H-mordenite and partially dealuminated HY faujasite are very effective for the alkylation of aniline with propylene.

19 Claims, No Drawings

ALKYLATION OF AROMATIC AMINES WITH OLEFINS ON PARTIALLY DEALUMINATED ZEOLITES

This commonly assigned application is a continuation-in-part of U.S. Ser. No. 796465 having a filing date of Nov. 8, 1985 now U.S. Pat. No.4,740,620, the subject matter of which is incorporated by reference and a continuation-in-part of U.S. Ser. No. 848,000 having a filing date of Apr. 2, 1986 now abandoned, the subject matter being incorporated by reference.

TECHNICAL FIELD

This invention relates to a catalytic process for producing alkylated aromatic amines by the reaction of an aromatic amine with an olefin over a highly acidic partially dealuminated zeolite.

BACKGROUND OF THE INVENTION

Processes for alkylating a variety of alkylatable aromatic compounds by contacting such aromatic compounds with a hydrocarbon radical providing source such as an olefin or alcohol are widely known. Typically, alkylatable aromatic compounds are mononuclear aromatic compounds, including those substituted with a hydroxyl, amine or an ether group. The alkylation has been carried out in the presence of homogeneous and heterogeneous catalyst systems.

Ring alkylated aromatic amines have been some of the products produced by alkylation procedures. Ring alkylated aromatic amines have a variety of uses in chemical synthesis. Some of the early uses were intermediates for substituted isocyanates, herbicidal compositions, dyestuffs and textile auxiliary agents. More recently aromatic amines have been utilized as chain lengthening components in polyurethane systems. These are commonly referred to as chain extenders.

Representative references which illustrate some of the early processes in forming ring alkylated aromatic amines are as follows.

British Patent No. 414,574 discloses the reaction of aniline with various olefins, e.g., cyclohexene and alcohols, e.g., butanol in the presence of a neutral or weakly acidic catalyst system commonly referred to as hydrosilicates at temperatures from 200°–270° C. Ortho and para-cyclohexylaniline, N-cyclohexylaniline, N-butylaniline and para-methyl-ortho-cyclohexylaniline and N-cyclohexyl-para-toluidine are listed as representative products.

British Patent No. 846,226 discloses ring alkylation of aromatic amines with olefins using active, substantially neutral bleaching earths of the montmorillonite type as a catalyst.

West Germans No. AS 1,051,271 discloses the ring alkylation of aniline with an olefin, e.g., ethylene, in the presence of kaolin or in the presence of aluminum and aluminum alloys. Alkylation with higher olefins, e.g., propylene, butylene, etc., was carried out in the presence of Friedel-Crafts catalysts or bleaching earths under liquid phase conditions at temperatures from 150°–350° C. Examples of catalytic systems included aluminum chloride, zinc chloride, boron trifluoride, sulfuric acid, phosphoric acid and bleaching earth. Ring alkylation at the ortho-position was predominant, although other products such as the di-and tri-alkylated aniline product were produced.

In an article by Zollner and Marton, Acta Chim. Hung. Tomus 20. 1959 (Pages 321–329), the vapor phase alkylation of aniline with ethanol was effected in the presence of aluminum oxide.

U.S. Pat. Nos. 3,649,693 and 3,923,892 discloses the preparation of ring alkylated aromatic amines by reacting an aromatic amine with an olefin in the presence of aluminum anilide, optionally including a Friedel-Crafts promoter. Reaction products include 2-ethylaniline, and 2,6-diethylaniline.

Stroh, et al., in U.S. Pat. Nos. 3,275,690; 2,762,845, Japanese Sho No. 56-110652, and, as mentioned previously, West German No. AS 1,051,271, disclose various processes for preparing alkylated aromatic amines by reacting an aromatic amine with an olefin in the presence of Friedel-Crafts catalysts as well as a combination of the Friedel-Crafts catalysts in the presence of halogen compounds combined with aluminum. Representative reaction products included 2-cyclohexylaniline, diethyltoluenediamine, diethylaniline, diisopropylaniline and mono-tert-butylaniline.

The art, e.g., Netherlands Application No. 6,407,636, has recognized that alkylation of various aromatic and heterocyclic compounds can be carried out in the presence of a zeolite having a pore size from 6-15 Angstroms wherein active cation sites are obtained with an exchangeable metal or hydrogen cations in their ordered internal structure. Alkylating agents include olefins having from 2 to 12 carbon atoms, alkyl halides such as propylbromide and ethylchloride; and alkanols, such as, methanol, ethanol, and propanol. Various compounds were suggested as being suited for alkylation and these include both the heterocyclic and aromatic ring compounds. For aromatic amine alkylation it was suggested that a zeolite with a disperse distribution of acidic sites should be utilized. It was believed the highly acidic zeolite catalysts, which have a high density of acidic sites, may bind the amine to the catalyst and block the pore structures. In Example 1, aniline was alkylated with propylene using sodium zeolite X having a pore size of 13 Angstroms; numerous alkylated amines were produced. Example 3 shows alkylation of diphenylamine with cyclohexene using a rare earth exchanged 13 X zeolite. Again, numerous ring alkylated products were produced and high temperatures, e.g. 300° C. and above, apparently were required to weaken the amine-acid bond.

French Patent No. 1,406,739, which is equivalent to Netherlands Application No. 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a 13X molecular sieve which has undergone a partial exchange with rare earth metals and having a pore size of 13A°.

The following patents show the use of dealuminated or high silica zeolites for a variety of hydrocarbon conversion processes. The patents are as follows.

U.S. Pat. No. 3,506,400 discloses the preparation of crystalline alumino silicates having high silica to alumina mole ratios by heat treatment of the zeolite in the presence of water to effectuate removal of a substantial portion of alumina from the zeolite structure. These zeolites, which contained a higher silica to alumina ratio, were shown to be effective for catalytic cracking.

U.S. Pat. No. 3,761,396 discloses the conversion of hydrocarbons in the presence of a dealuminated zeolite, the dealumination being accomplished by extracting framework aluminum from the crystalline molecular sieve using acetylacetone as the extracting agent. The examples show the use of partially dealuminated zeolites as being effective catalysts for the alkylation of benzene with propylene.

U.S. Pat. No. 3,937,791 discloses various hydrocarbon conversion processes using a dealuminated zeolite having framework aluminum extracted therefrom. Some of the early techniques for dealumination involved treatment with acid or chelating agents such as ethylenediamine tetraacetic acid (EDTA); however, it was preferred that chromium chloride be used as the free agent for removing framework aluminum because it leaves a material which is more porous than obtained with EDTA.

U.S. Pat. No. 3,493,519 discloses a hydrothermally stable catalyst system for hydrocarbon conversion. The catalyst is prepared by calcining an ammonium Y crystalline alumino-silicate in the presence of a rapidly-flowing steam and base exchange the steam product with an ammonium salt and then treating the exchange product with a chelating agent for extracting framework aluminum. The catalyst was suggested as being suited for alkylation, dealkylation, isomerization, disproportionation, translkylation and other types of hydrocarbon conversion.

U.S. Pat. Nos. 3,178,365; 3,281,483; 4,259,537; 4,395,372 and 4,393,262 disclose the alkylation of aromatic hydrocarbon compounds with an olefin in the presence of various crystalline alumino-silicates, such as crystalline alumino-silicates having undergone previous transformation by reaction with a nitrogen oxide containing compound, a hydrogen mordenite, a ZSM catalyst exchanged with a VIa metal; crystalline alumino-silicates promoted with sulfur dioxide and dealuminated zeolites. The dealuminated and high silica zeolites (ZSM) are disclosed as having particular activity for the alkylation of benzene.

Although the prior art has disclosed that a variety of catalytic systems can be utilized in the alkylation of aromatic hydrocarbons and aromatic amines, the art also teaches that a variety of reaction products are produced, including both ortho and para-isomers of mononuclear aromatic amines as well as, mono, di and tri alkyl substituted amines. In addition, the prior art teaches that neutral to weakly acidic catalysts are preferred for effecting ring alkylation of the aromatic amines. Even though the prior art has suggested preferred catalytic systems such systems also involve batch, liquid phase operation which may be difficult to operate over an extended period of time, and tend to give more para product. In addition, many of the processes suffer from poor conversion, poor reaction rate and an inability to produce high ortho to para isomer ratios at high conversion.

SUMMARY OF THE INVENTION

This invention pertains to an improved process for effecting alkylation of aromatic amines and preferably ortho-alkylation of aromatic amines that contain at least one hydrogen adjacent to an amino group and at least one hydrogen on either an amine nitrogen or a ring carbon not adjacent to an amino group. These compounds are typically represented by the formulas:

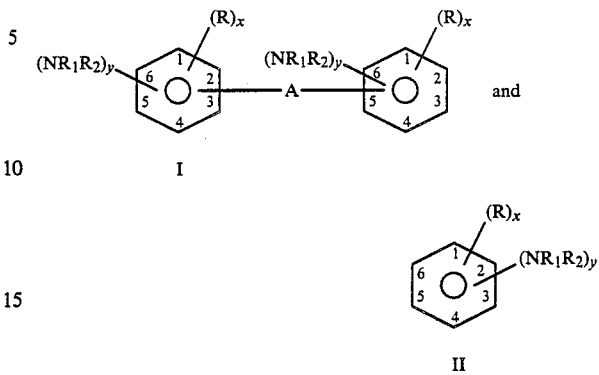

where R is $C_{1-10}$ alkyl, phenyl, alkoxy, ester or nitrile; $R_1$ and $R_2$ are each selected from hydrogen or $C_{1-10}$ alkyl; x is 0 to 2; A is $C_{0-4}$ alkylene, y is 1 or 2 except one y in formula I can be zero and provided not more than one R is ester, alkoxy or nitrile. Alkylation of the aromatic amine is effected by contacting the aromatic amine with an aliphatic, acyclic or cyclic olefin in the presence of a highly acidic (acidity factor greater than 0.3 mm ammonia irreversibly absorbed at 200° C. per gram of catalyst at 200° C.) partially dealuminated zeolite.

Some of the advantages associated with this invention include:

an ability to give higher selectivity to ring alkylated products.

an ability to selectively produce alkylated aromatic amines where the alkyl group is in the ortho position, i.e., ortho relative to the amine group, as opposed to the para position;

an ability to effect alkylation at high conversion;

an ability to effect ring alkylation of aromatic amines at high rates; and an ability to utilize a fixed bed catalytic reactor lending itself to continuous vapor, liquid, and mixed phase operation;

DETAILED DESCRIPTION OF THE INVENTION

As stated above ring alkylation of aromatic amines which can be selectively orthoalkylated according to this invention are represented by the formulas:

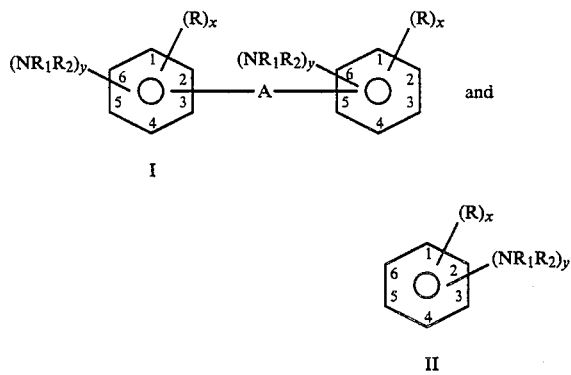

where R is $C_{1-10}$ alkyl or phenyl, alkoxy, ester, nitrile; $R_1$ and $R_2$ are each selected from hydrogen or $C_{1-10}$ alkyl; x is 0 or 2; A is $C_{0-4}$ alkylene, y is 1 or 2 except one y in formula I can be zero and provided not more than one R group is alkoxy, ester or nitrile, and the positions of substituents are such that there is at least one ring hydrogen adjacent to an amino group and (i) at least one hydrogen on an amino group (i.e. at least one $R_1$ or $R_2$ is hydrogen) or (ii) at least one ring hydrogen not adjacent to an amino group.

As shown in the above formulas, the aromatic amine can be monoamino or diamino substituted where the amine substituent is on the aromatic ring. Further, the aromatic amine can be substituted with a variety of substituents which are nonreactive with the olefin in the alkylation reaction. Examples of nonreactive substituents include alkylamino where the alkyl portion has from 1-8 carbon atoms, such as N-ethyl, N-propyl and N-tert-butyl; alkyl where the alkyl substituent has from 1-6 carbon atoms, e.g. ethyl, propyl, tert-butyl and cyclohexyl, methylcyclohexyl; alkoxy, i.e., aliphatic ether, where the carbon content is from 2-6 carbon atoms, and ester, where the carbon content is from about 2-6 carbon atoms.

Many of the amines included within formulas I and II have hydrogen atoms which are reactive in positions ortho and para to an amino group. When both of these hydrogens are reactive to alkylation, one has the ability with this catalyst system to selectively produce one isomer in favor of another. In the case of aromatic amines having hydrogen atoms which are reactive in both positions the ortho position may be more reactive, but the para alkylated product may be more thermodynamically stable. In most of the prior art systems, one could not simultaneously obtain high conversion of aromatic amine and high selectivity to an ortho-alkylated amine. If one went to high conversion of aromatic amine, one obtained a higher proportion of the para-isomer.

Specific examples of such aromatic amines suited for ortho alkylation include aniline, toluidines, 2,3-, 2,4-, and 3,4-xylidines, toluenediamines, xylidenediamine, methylenedianiline, N-ethyl aniline, N-propyl aniline, (N-propylamino)aminotoluene, isobutylaniline, phenyl aniline, phenylenediamines and 2-methyl-4-benzylaniline. Aromatics amines particularly well suited for alkylation according to this invention are those having active hydrogen atoms in positions ortho and para to an amino group such as aniline, orthotoluidine, 2,6-toluenediamine and ortho-phenylenediamine.

Alkylating agents used for practicing the invention are mono aliphatic, acyclic and cyclic olefins such as ethylene, propylene, butene isobutylene, isoamylene, cyclohexene, 1-methylcyclohexene, 1-methylcyclopentene. Typically, these olefins will have from 2 to 12 carbon atoms in the structure and preferably 2-6 carbon atoms. For some aromatic amines, the choice of alkylating agents may be limited due to steric effects from groups attached to the amino group and/or adjacent on the ring to the position which is ortho to the amino group.

In the alkylation of aromatic amines the molar ratio of olefin to aromatic amine can influence the selectivity of the reaction. In those cases where the aromatic amine can be alkylated in positions ortho and para to an amine group, the molar ratio of olefin to aromatic amine influences, to some degree, whether the ring alkylation is ortho to the amine or para to the amine. Typically olefin to amine molar ratios will range from about 0.5 to 20 moles olefin per mole of aromatic amine and preferably 1-8 moles olefin per mole of aromatic amine.

The catalysts used in the reaction of the present invention are those crystalline molecular sieves which are solid phase and have high acidity. They are categorized as being partially dealuminized zeolites and have a silica to alumina ratio higher than the original parent zeolite. As a result partially dealuminated acidic molecular sieves have greater catalytic activity to effect ring-alkylation of the aromatic amine in high conversion (based upon amine) and in high selectivity than the parent zeolite. The crystalline molecular sieves include crystalline alumino-silicates, commonly referred to as zeolites, and they can be of both natural and synthetic material. Some examples of the zeolites are faujasites such as X and Y, L, gmelinite, erionite, mordenite, offretite, omega, and chabazite. When initially prepared, the cation in the crystalline alumino-silicate usually is an alkali metal, typically sodium rendering the catalyst weakly acidic. This ion should be exchanged in sufficient proportion, generally in excess of 60%, with an acidic ion such as hydrogen, a rare earth metal, e.g. lanthanum, cerium, praseodymium; or some of the transition metals such as nickel, copper, chromium and the like to achieve the desired acidity for the practice of this invention. The substitution of various ions for the sodium ion, particularly rare earth metals and hydrogen, alters the acidity of the zeolite thus making it more reactive and catalytically effective for ring alkylation of the aromatic amine.

The dealuminated catalysts used in the reaction of the present invention are those crystalline molecular sieves which are solid phase and have an acidity factor of at least 0.30 and preferably at least 0.6. As a result these highly acidic dealuminated molecular sieves have sufficient catalytic activity to effect ring-alkylation of the aromatic amine in high conversion (based upon amine) and in high selectivity. Sufficient alkali metal must be exchanged with appropriate acidic cations to render the crystalline molecular sieve acidic as defined by an acidity factor. This factor is determined by an ammonia absorption/desorption technique which involves treating the catalyst with ammonia at room temperature and then desorbing by heating to a temperature from ambient to 200° C. at 10°/minute, then holding at 200° C. for 2 hours. The amount of ammonia irreversibly adsorbed at 200° C. is indicative of acidity and indicative of the strength of the amine/acid bond. An acidity factor of 0.30 millimoles ammonia irreversible adsorbed per gram of catalyst at 200° C. is minimally necessary to obtain high catalytic activity and to obtain a high ortho to para isomer ratio at high conversion with those aromatic amines having hydrogen atoms which are reactive in both the ortho or para positions.

The zeolites are porous materials with the pores having generally uniform molecular dimensions. Cavities or cages are formed in the zeolite and are conducted by channels of generally defined diameter. For the practice of this invention the cage diameter should be sufficiently large to permit the molecules to effectively enter the interior of the alumino-silicate for reaction and to exit as final product. Typically the pore size will range from about 6 to 15 Angstroms but the size of the pore required can vary depending upon the product being produced. An ethyl substituent can be prepared from a smaller pore zeolite than can a tert-butyl or cyclohexyl substituent. It also follows that an alkyl substituted mononuclear aromatic amine can be produced with a smaller pore size zeolite than can an alkyl substituted polynucleararomaticamine. If the pore size is too small or tortuous to permit entry of the reactants, conversion will be low at low temperatures and catalytic activity will be limited to surface catalysis. Higher temperatures may be required to enhance molecular diffusion in the framework of the zeolite.

The partial dealumination of zeolitic materials in combination with increasing acidity has been found to enhance the alkylation of the aromatic amine with the olefin without interfering with the selectivity of the catalyst system. In fact, selectivity is enhanced in many cases even at high conversion. Higher ring alkylation as against N-alkylation is obtained at high conversions. Among the ring alkylated products, the selectivity to ortho-alkylated products is enhanced. With respect to partially dealuminated zeolites, the partial dealumination improves catalyst life presumably because the stability of the zeolite is improved by increasing the silica to alumina ratio. By partial dealumination it is meant that the zeolite is treated with a dealuminating agent such as a chelating agent or acid for the purpose of removing aluminum atoms from the zeolite structure. Typically the proportion of aluminum removed is sufficient to effect removal of 10-80% from the total alumina ($Al_2O_3$ by weight) present in the zeolite material. For example, mordenite normally has an Si to Al molar ratio of about 5:1. The Si to Al molar ratio for partially dealuminated mordenite should be from 6 to 100:1 with preferred molar ratios of 8 to 20:1. The silicon to aluminum molar ratio of a Y zeolite is about 2.2:1. The Si to Al ratio for a partially dealuminated Y zeolite should be at least from 2.5 to 50:1 with a preferred Si to Al molar ratio of 2.5 to 15:1. Excessive dealumination can also alter catalyst structure and performance. For a given zeolite and reactants, there can be an optimum level of dealumination which can readily be determined with a small amount of testing.

There are several techniques available for removing aluminum atoms from the structure and some involve the treatment of the zeolite material with a chelating agent such as acetyl acetonate, ethylenediaminetetracetic acid, or by treatment with a mineral acid, e.g. hydrochloric acid. When the catalyst is prepared by acid treatment it is preferred to first ammonium exchange the zeolite and then treat with concentrated acid for a few hours. If the zeolite is not in the H-form when dealuminated, dealumination may be insufficient or the cage structure may be destroyed in achieving dealumination.

Subsequent to the partial dealumination, the zeolite should not be subjected to any treatment, such as hydrothermal treatment, which can have a detrimental affect on its catalytic properties. For example, deep bed calcination or calcination in a wet air stream can extract framework aluminum from the zeolites and alter their acidic properties substantially; and in some cases this treatment is known to have a detrimental effect on their catalytic properties.

The alkylation of aromatic amines to effect ring alkylation of the aromatic amine can be carried out in a fixed bed reactor with the reactants being fed downflow or upflow through the reactor. The reaction can also be carried out in a stirred autoclave. Temperatures from 50 to 425° C. and pressures of from near atmospheric to 3000 psig are utilized. Although conversion of an aromatic amine to a ring alkylated product may be greater at temperatures near the upper end of the range specified, the degree of alkylation in the ortho-position as opposed to the para-position may be greatly reduced and olefin polymerization may occur. Higher conversions obtained at high temperatures may tend to form higher concentrations of the para-isomer. Thus, to obtain a reaction product with the highest ortho to para-isomer ratio the reaction temperature might have to be controlled to produce a conversion range that will give the highest ortho to para-isomer ratio.

Reaction time is an important factor in achieving high selectivity to an ortho-alkylated product as opposed to a N and/or para-alkylated product, i.e., the alkyl group being attached to the amino group or in the four position. Broadly, the reaction time can be expressed as a liquid hourly space velocity (LSV) of feed components to the reactor and typical values for liquid hourly space velocity based on aromatic amine are from 0.05 to 6 hours$^{-1}$. If one is operating at relatively high temperatures for the alkylation reaction, a relatively higher LHSV may be used to get reasonable conversions. In contrast, a lower LHSV permits one to obtain high conversion at lower temperatures. Often a combination of temperature, pressure and LHSV may be chosen to get an appropriate isomer mix at high conversion.

Liquid phase, vapor phase or mixed phase conditions may be utilized in the practice of the invention and the process may be carried out on a batch or continuous basis. When a batch process is utilized the proportion of aromatic amine is from about 5 to 100 weight parts per weight part catalyst.

The following examples are provided to illustrate various embodiments of the invention and are not intended to restrict the scope thereof.

EXAMPLE 1

A sample of 1/16" H-mordenite Z-900H extrudate from the Norton Company was partially dealuminated by treatment with hydrochloric acid and ammonium chloride solution. The procedure involved first refluxing 40 g of the H-mordenite in 0.17 N HCl and 2M ammonium chloride solution for 4 hours (total solution volume 600 ml). The catalyst was then washed twice by refluxing in 1 liter of doubly distilled water for an hour interval and then dried at 150° C. for 3 hours under vacuum. By the X-ray fluorescence analysis, the Si/Al mole ratio of this partially dealuminated H-mordenite was found to be 8.14. The original zeolite had a Si/Al ratio of about 5-6.5 and X-ray diffraction pattern of the partially dealuminated H-mordenite showed no substantial loss of crystallinity. It had an acidity factor greater than 0.6 mm ammonia absorbed per gram of zeolite.

Alkylation of aniline was effected by charging 11.5 gm of the partially dealuminated mordenite into a half inch O.D. 304 stainless steel tube. A preheating zone of about 5.4 cc Vycor glass was also provided above the catalyst in the same tube. This tube was slowly heated in a furnace with the rate of about 2-5° C. per five minutes to 305° C. under a flow of nitrogen of about 200-300 cc/min and was kept at 305° C. for two hours. After this time period, the catalyst was cooled to room temperature. Aniline and propylene were then pumped as liquids; the reactor temperature was brought to 230° C. and its pressure to 938 psia. The flow rate of aniline was 1.25 cc/hr and of propylene 1.85 cc/hr. The aniline to propylene molar ratio was 0.5. The effluent from the reactor was collected and purged free of residual propylene. An aliquot of this effluent was analyzed by gas chromatography and showed the following results:

| | |
|---|---|
| Aniline Conversion (%) | 76 |
| Product Selectivity (mole %) | |
| N—isopropylaniline | 15.7 |
| 2-isopropylaniline | 78.6 |
| 4-isopropylaniline | 0.9 |
| N,2-diisopropylaniline | 0.5 |
| 2,6-diisopropylaniline | 2.7 |

The data shows high conversion to ring alkylated aniline and excellent selectivity to the ortho product. It is also important to note that very little dialkyl substituted material was formed.

EXAMPLE 2

Several alkylation runs were carried out with aniline and propylene using the catalyst and procedure of Example 1. The results are set forth in Table 1 and show the effect of temperature and space velocity.

TABLE 1
ANILINE ALKYLATION WITH PROPYLENE ON PARTIALLY DEALUMINATED H—MORDENITE

| Run | 1 | 2 | 3 | 4 |
|---|---|---|---|---|
| Aniline Conversion (%) | 48 | 63 | 76 | 73 |
| Selectivity (mole %) | | | | |
| N—isopropylaniline | 20.8 | 17.1 | 15.7 | 12.6 |
| 2-isopropylaniline | 76.1 | 78.6 | 78.6 | 78.8 |
| 4-isopropylaniline | 1.4 | 1.1 | 0.9 | 1.1 |
| N,2-diisopropylaniline | 0.2 | 0.3 | 0.5 | 1.2 |
| 2,6-diisopropylaniline | 0.9 | 1.7 | 2.7 | 4.6 |
| Unknowns | 0.6 | 1.2 | 1.5 | 1.8 |
| T (°C.) | 210 | 231 | 230 | 248 |
| P (PSIA) | 931 | 940 | 938 | 940 |
| LHSV (hr$^{-1}$) | 0.125 | 0.125 | 0.0625 | 0.0625 |
| Aniline/Propylene (mole ratio) | 0.5 | 0.5 | 0.5 | 0.1 |

*LHSV is defined on the basis of aniline flow rate at room temperature, i.e.,
$$LHSV = \frac{\text{volumetric flow rate of aniline}}{\text{volume of catalyst bed}}$$

The data shows that temperatures from about 210°-250° C. result in good conversion to ring alkylated aniline and selectivities exceeded about 75%. Less than 6% diisopropyl aniline was produced in all cases.

EXAMPLE 3

The procedure of Example 1 was repeated with the exception that various catalytic systems were compared to the partially dealuminated mordenite. These catalysts include gamma alumina; highly acidic (acidity factor greater than 0.6) H-mordenite; highly acidic (acidity factor greater than 0.6) H-Y faujasite and silica-alumina. The results are set forth in Tables 2 and 3.

TABLE 2
REACTION PRODUCTS OF ANILINE ALKYLATION WITH PROPYLENE

| Catalyst | PDHM** | γ - Al$_2$O$_3$ |
|---|---|---|
| Aniline Conversion (%) | 76 | 80 |
| Selectivity (mole %) | | |
| N—isopropylaniline | 15.7 | 5.4 |
| 2-isopropylaniline | 78.6 | 63.5 |
| 4-isopropylaniline | 0.9 | 0.4 |
| 2,6-diisopropylaniline | 2.7 | 20.1 |
| 2,4,6-triisopropylaniline | 0.0 | 0.5 |
| Unknowns | 2.4 | 10.2 |
| *Total Unknowns | 3 | 11 |
| T (°C.) | 230 | 351 |
| P (PSIA) | 938 | 872 |
| LHSV (hr$^{-1}$) | 0.0625 | 0.125 |

TABLE 2-continued
REACTION PRODUCTS OF ANILINE ALKYLATION WITH PROPYLENE

| Catalyst | PDHM** | γ - Al$_2$O$_3$ |
|---|---|---|
| N/R | ½ | 1/10 |

*Compounds which give a peak in chromatogram and have not been identified.
**PDHM: Partially dealuminated H—mordenite, Example 1.

TABLE 3
ALKYLATION OF ANILINE WITH PROPYLENE ON VARIOUS CATALYSTS

| Catalyst | PDHM* | 13% Al$_2$O$_3$/SiO$_2$ | H—Y |
|---|---|---|---|
| Approximate Aniline Conversion (%) | 63 | 61 | 60 |
| Selectivity (%) | | | |
| N—isopropylaniline | 17.1 | 28.2 | 26.0 |
| 2-isopropylaniline | 78.6 | 56.5 | 55.2 |
| 4-isopropylaniline | 1.1 | 2.4 | 3.7 |
| N,2-diisopropylaniline | 0.3 | 7.0 | 4.7 |
| 2,6-diisopropylaniline | 1.7 | 9.3 | 11.5 |
| 2,4,6-triisopropylaniline | 0.00 | 0.01 | 0.01 |
| Operating Variables | | | |
| T (°C.) | 231 | 252 | 228 |
| P (PSIA) | 940 | 962 | 913 |
| LHSV (hr$^{-1}$) | 0.125 | 0.120 | 0.250 |
| Aniline/Propylene (mole ratio) | 0.5 | 0.5 | 0.1 |

*PDHM: partially dealuminated H-mordenite, Example 1.

From Tables 2 and 3, the alkylation of aniline with propylene on highly acidic partially dealuminated H-mordenite (PDHM) was found not only very active but also highly selective towards the formation of 2-isopropylaniline. Under proper operating conditions, this catalyst was found not to deactivate with time on stream for the period tested.

For the aniline-propylene reaction, the superior activity and selectivity of the PDHM catalyst, with respect to the other catalysts is also demonstrated. Table 2 shows that high levels of conversions are achieved on PDHM at temperatures which are about 100° C. lower than those for the Y-Al$_2$O$_3$ catalyst. Moreover, the number and quantity of unknown compounds formed is substantially less for the run using PDHM than for the run using Y-Al$_2$O$_3$. In Table 3, the performance of PDHM is reported for approximately the same pressure, LHSV, and aniline/propylene mole ratio as that used for the 13% Al$_2$O$_3$/SiO$_2$ sample. However, PDHM achieves the same level of aniline conversion at a temperature about 21° C. lower than 13% Al$_2$O$_3$/SiO$_2$.

It is important to compare the formation of para-isomers using PDHM with the other active catalysts. At the same levels of aniline conversion, the amount of 4-isopropylaniline formed on SiO$_2$/Al$_2$O$_3$ containing 13% Al$_2$O$_3$ is about twice of the PDHM, and on H-Y, it is about three times that on the PDHM (Table 3).

For the same level of aniline conversions, PDHM is much more selective towards the monosubsitution of propylene in the ortho position on aniline. For example, in Table 2, the selectivity to ortho-isopropylaniline for the PDHM is about 79% while that for Y-Al$_2$O$_3$ is about 64%. In Table 3, the selectivity for 13% Al$_2$O$_3$/SiO$_2$ is about 57% and for H-Y about 55% while the selectivity for the PDHM run is significantly higher at about 79%. From Table 3 it is also seen that the amount of N-alkylation for the PDHM run is much less than for the runs using 13% Al$_2$O$_3$/SiO$_2$ or H-Y.

EXAMPLE 4

A batch of partially dealuminated H-mordenite was prepared from Zeolon 900 H with the procedure being similar to that described in Example 1. The alkylation of aniline with propylene was also studied in accordance with Example 1 by charging 10.13 gm of this partially dealuminated mordenite (PDHM) into a half inch O.D. 304 stainless steel tube. The results of the above run were compared with a run using the parent starting material Zeolon 900 H (HM). The run with HM was made by using 11.73 gm of material. The results from the two runs are listed in tables 4 and 5.

TABLE 4

Comparison of the Activity of Catalysts HM and PDHM

| Catalyst | Parent HM | PDHM |
|---|---|---|
| Aniline Conversion (%) | 24 | 66 |
| Selectivity (mole %) | | |
| N—isopropylaniline | 22.8 | 10.0 |
| 2-isopropylaniline | 67.4 | 80.8 |
| 4-isopropylaniline | 3.0 | 2.3 |
| N,2-diisopropylaniline | 2.5 | 1.1 |
| 2,6-diisopropylaniline | 3.0 | 4.4 |
| Unknowns | 1.3 | 1.4 |
| T(°C.) | 250 | 250 |
| P (psia) | 920 | 930 |
| LHSV (hr$^{-1}$) | 0.068 | 0.067 |
| Aniline/Propylene (mole ratio) | 0.5 | 0.5 |

TABLE 5

Selectivities Achieved Using HM; and PDHM

| Catalyst | Parent HM | PDHM | |
|---|---|---|---|
| Aniline Conversion (%) | 24 | 17 | 44 |
| Selectivity (mole %) | | | |
| N—isopropylaniline | 22.8 | 14.5 | 12.2 |
| 2-isopropylaniline | 67.4 | 82.4 | 82.5 |
| 4-isopropylaniline | 3.0 | 2.1 | 2.3 |
| N,2-diisopropylaniline | 2.5 | 0.0 | 0.5 |
| 2,6-diisopropylaniline | 3.0 | 0.9 | 2.0 |
| Unknowns | 1.0 | 0.2 | 0.5 |
| T(°C.) | 250 | 212 | 231 |
| P (psia) | 920 | 867 | 926 |
| LHSV (hr$^{-1}$) | 0.068 | 0.136 | 0.128 |
| Aniline/Propylene (mole ratio) | 0.5 | 0.5 | 0.5 |

The relevant results from Tables 4 and 5 are:

From Table 4 it is seen that the activity of the HM catalyst is significantly lower than that of PDHM. At these operating conditions, the aniline conversion achieved using HM is only 24% as compared to 66% using PDHM.

Since data for each catalyst at the same conversion level, temperature, and pressure are not available at this time, a precise comparison of the selectivities achieved using these different materials can not be made. There is, however, enough data available to draw some conclusions about the relative selectivities of HM, and PDHM catalysts. The following observations can be made from Table 5:

A significant decrease in the selectivity to N-isopropylaniline ad 4-isopropylaniline and a significant increase in selectivity to 2-isopropylaniline are observed from PDHM relative to HM.

The ratio of 2-isopropylaniline to N-isopropylaniline is 'for HM compared to ≠for PDHM.

The amount of 2,6-diisopropylaniline formed on PDHM is considerably less than that on HM.

The selectivity to N-2-diisopropylaniline and unknown is higher for HM.

Thus, both ring alkylation and ortho-alkylation are increased when using a partially dealuminated form of H-Mordenite.

EXAMPLE 5

A highly acidic (acidity factor greater than 0.9) partially dealuminated HY zeolite was prepared by treatment of LZY62 from Union Carbide by slow addition of ethylene diamine tetraacetic acid (EDTA). The resulting crystalline material had a Si/Al ratio of 9.0.

The effect of Si/Al ratio of HY was determined by testing samples of LZY62 (Si/Al=2.42), and two partially dealuminated LZY62 samples (Si/Al=3.2 and 9.0). Partial dealumination of LZY62 results in a significant improvement in the activity for aniline alkylation with propylene. No significant loss in selectivity to ortho-alkylated product was observed.

| Relative Activity (moles/cc/hr) | Si/Al ratio |
|---|---|
| 1 | 2.4 |
| 1.4 | 3.2 |
| 2.7 | 9.0 |

It should be noted that activity increased substantially with increased silica-alumina mole ratio.

What is claimed is:

1. In a process for producing an alkylated aromatic amine by contacting an aromatic amine with an olefin in the presence of a zeolitic catalyst system, the improvement wherein enhanced activity and selectivity to ortho-alkylated amine product is obtained which comprises contacting the aromatic amine and olefin with a highly acidic zeolite having a acidity factor such that at least 0.3 mm ammonia are irreversibly absorbed at 200° C. per gram of catalyst for 2 hours and which has been partially dealuminated in an amount sufficient to remove at least 10% by weight by the original alumina from the zeolite.

2. The process of claim 1 wherein said aromatic amine contains at least one ring hydrogen adjacent to an amino group and at least one hydrogen on an amine nitrogen or on a ring carbon not adjacent to an amino group and is represented by one of the formulas

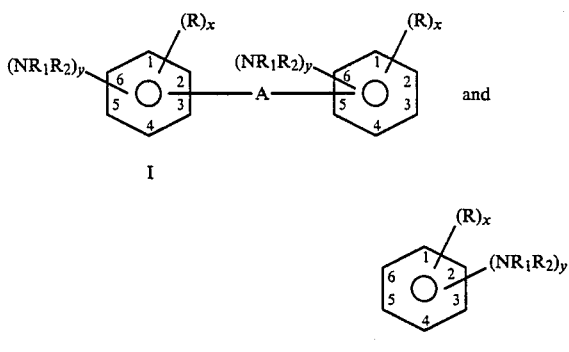

where R is C$_{1-10}$ alkyl, phenyl, halogen, alkoxy, ester or nitrile; R$_1$ and R$_2$ are each selected from hydrogen or C$_{1-10}$ alkyl, x is 0 to 2, A is C$_{0-4}$ alkylene, Y is 1 or 2 except one y in formula I can be zero and provided not more than one R is alkoxy, ester or nitrile.

3. The process of claim 1 wherein the cation in said zeolite is mainly the hydrogen ion or is ion exchanged with rare earth metals and the acidity factor is at least 0.6.

4. The process of claim 2 wherein said olefin is a $C_2$ to $C_{12}$ aliphatic, acyclic or cyclic olefin.

5. The process of claim 3 wherein said reaction temperature is from 50° to 450° C.

6. The process of claim 4 wherein the reaction pressure is from about atmospheric to 3000 psig.

7. The process of claim 5 wherein the partially dealuminated zeolite has a silica to alumina mole ratio of 8-20:1.

8. The process of claim 6 wherein the molar ratio of olefin to aromatic amine is from about 0.5-20:1.

9. The process of claim 7 wherein the olefin is a $C_2$ to $C_6$ olefin.

10. The process of claim 8 wherein said partially dealuminated zeolite is selected from a group consisting mordenite, offretite, X, Y, omega and L.

11. The process of claim 9 wherein said aromatic amine is represented by formula II.

12. The process of claim 10 wherein $R_1$ and $R_2$ are hydrogen.

13. The process of claim 11 wherein R is methyl and x is 0 or 1.

14. The process of claim 12 wherein said olefin is propylene.

15. The process of claim 14 wherein said aromatic amine is aniline.

16. The process of claim 13 wherein said zeolite is a dealuminated hydrogen ion exchanged mordenite.

17. The process of claim 16 wherein said mordenite has a silica to alumina mole ratio of 8-20:1.

18. The process of claim 12 wherein said zeolite is a partially dealuminated hydrogen exchanged Y zeolite.

19. The process of claim 5 wherein said zeolite is H-mordenite, said aromatic amine is aniline and said olefin is propylene.

* * * * *